United States Patent [19]

Lerner et al.

[11] Patent Number: 5,612,380

[45] Date of Patent: Mar. 18, 1997

[54] METHOD FOR SLEEP INDUCTION

[75] Inventors: Richard A. Lerner; Dale Boger, both of La Jolla; Ben Cravatt; Gary E. Siuzdak, both of San Diego; Steven J. Henriksen, Solana Beach, all of Calif.

[73] Assignee: The Scripps Research Institute, La Jolla, Calif.

[21] Appl. No.: 369,036

[22] Filed: Jan. 5, 1995

Related U.S. Application Data

[63] Continuation-in-part of Ser. No. 314,583, Sep. 27, 1994, abandoned.

[51] Int. Cl.⁶ .................................................. A61K 31/16
[52] U.S. Cl. ......................... 514/627; 514/625; 514/923
[58] Field of Search ................................ 514/625, 627, 514/923

[56] References Cited

U.S. PATENT DOCUMENTS

| | | | |
|---|---|---|---|
| 4,729,834 | 3/1988 | Itoh | 210/670 |
| 4,851,431 | 7/1989 | Yehuda | 514/560 |
| 5,163,982 | 11/1992 | de Andrade Bruuning | 55/67 |

OTHER PUBLICATIONS

Arafat, et al., "Identification of Fatty Acid Amides in Human Plasma", *Life Sciences*, 45: 1679–1687 (1989).

Wakamutsu et al., "Isolation of Fatty Acid Amide as an Angiogenic Principle from Bovine Mesentery", *Biochem. and Biophys. Research Comm.*, 168: 423–429 (1990).

Taranova, et al., "Lipid peroxidation of rat brain synaptosomes in sleep disturbance", abstract No. 105:169775, Fiziol. Zh. SSSR im. I.M. Sechenova vol. 72, No. 8, pp. 1065–1068 (1986).

*Primary Examiner*—Kimberly Jordan
*Attorney, Agent, or Firm*—Donald G. Lewis

[57] ABSTRACT

Sleep may be induced by administration of fatty acid primary amides, including cis-9,10-octadecenoamide. Furthermore, sleep deprivation may be assayed by analyzing cerebrospinal fluid with respect to the presence of fatty acid primary amides, including cis-9,10-octadecenoamide. The presence of cis-9,10-octadecenoamide in cerebrospinal fluid is correlated with comparative sleep deprivation.

12 Claims, 7 Drawing Sheets

METHOD FOR SLEEP INDUCTION

STATEMENT OF GOVERNMENT RIGHTS

This invention was made with government support under a National Institutes of Health Shared Instrumentation grant No. 1 S10 RR07273-01. The government has certain rights in the invention.

This application is a continuation in part of Ser. No. 08/314,583, filed Sep. 27, 1994, now abandoned.

FIELD OF INVENTION

The invention relates to a method for inducing sleep and to an assay for sleep deprivation. More particularly, the invention relates to a method of inducing sleep by administration of fatty acid primary amides, including cis-9,10-octadecenoamide, and to a method for assaying sleep deprivation by analyzing cerebrospinal fluid with respect to fatty acid primary amides, including cis-9,10-octadecenoamide.

BACKGROUND

Sleep is a natural, periodic behavioral state during which the body rests itself and its physiological powers are restored. It is characterized by a loss of reactivity to the environment. During sleep, certain physiological processes of both the body and the brain function differently than they do during alert wakefulness. Normal sleep consists of at least two quite different behavioral states: synchronized sleep, during which the electroencephalogram consists of slow waves of high amplitude, and desynchronized sleep (DS) or activated sleep characterized by rapid eye movements (REM sleep), in which the electroencephalogram pattern is characterized by waves of high frequency and low amplitude. Synchronized sleep is further characterized by slow and regular respiration, by relatively constant heart rate and blood pressure, and by a predominance of delta waves. Synchronized sleep usually consists of four stages, followed by a period of activated sleep. Each cycle lasts between 80 and 120 minutes. In contrast, desynchronized sleep is further characterized by irregular heart rate and respiration, periods of involuntary muscular jerks and movements, and a higher threshold for arousal. Periods of desynchronized sleep last from 5–20 minutes and occur at about 90 minute intervals during a normal night's sleep.

Sleep deprivation can arise from any of a variety of sleep disorders and environmental factors. Insomnia is a common sleep disorder in which the individual is unable to initiate or maintain sleep. In the prior art, there is no known pharmacological method for inducing the full sleep cycle and no known method using biological samples for assaying sleep deprivation.

Diagnosis and treatment of a sleep disorder can be assisted by a verification and/or quantification of a patient's level of sleep deprivation. Unfortunately, it is often difficult to objectively quantify or verify the level of sleep deprivation reported by a patient. What is needed is a biochemical product generated by the patient that can be correlated with sleep deprivation.

Cerebrospinal fluid (liquor cerebrosinalis) is a clear, colorless fluid that circulates within the four ventricles of the brain and the subarachnoid spaces surrounding the brain and spinal cord. Cerebrospinal fluid originates as an ultrafiltrate of the blood secreted by the choroid plexus in the lateral third and fourth ventricles. Cerebrospinal fluid is also sometimes called neurolymph. After passing through the four ventricles and the subarachnoid spaces, cerebrospinal fluid is largely resorbed into the venous system via the arachnoid villi. Cerebrospinal fluid serves as a medium for the removal of catabolites, excretions, and waste materials from the tissues bathed by it. To date, no factor derived from cerebrospinal fluid has been reported to correlate with sleep deprivation. What is needed is a method for analyzing cerebrospinal fluid for identifying a biochemical factor generated by subject that correlates with sleep deprivation.

Since the seminal discovery of prostaglandins, there has been increasing recognition of the role of fatty acids and their derivatives in important physiological processes, e.g., B. Samuelsson, *Les Prix Nobel* 1982, pp. 153–174.

Fatty acid primary amides have not been associated in the prior art with sleep induction or for assaying sleep deprivation. Fatty acid primary amides have been identified as an angiogenic principle from bovine mesentery. (K. Wakamatsu, T. Masaki, F. Itoh, K. Kondo, K. Sudo, *Biochemical and Biophysical Research Communications* (1990): vol. 168 (2), pages 423–429. Fatty acid primary amides have also been identified in human plasma without any attribution of function. (E. Arafat, J. W. Trimble, R. N. Andersen, C. Dass, D. M. Desiderio, *Life Sciences* (1989): vol. 45(18) pages 1679–1687).

SUMMARY

From the cerebrospinal fluid of sleep-deprived cats, a molecule has been isolated, chemically characterized, and identified as cis-9,10-octadecenoamide. The structure of this compound was determined by mass spectrometry (MS), nuclear magnetic resonance spectroscopy (NMR), infrared spectroscopy (IR), gas chromatography (GC), thin layer chromatography (TLC), and chemical degradation procedures. Other fatty acid primary amides in addition to cis-9,10-octadecenoamide were identified as natural constituents of the cerebrospinal fluid of cat, rat, and man, indicating that these compounds compose a distinct family of brain lipids. Of particular significance, synthetic cis-9,10-octadecenoamide exhibited sleep-inducing properties when injected into rats. Together, these results teach that fatty acid primary amides represent a new class of biological signalling molecules.

One aspect of the invention is directed to methods for inducing subjects to sleep by the administration of fatty acid primary amides. Preferred fatty acid primary amides include an alkyl chain having an unsaturation and are represented by the following formula: $NH_2C(O)(CH_2)_{(6 \geq n \leq 11)}CH(CH_2)_{(8 \geq n \leq 5)}CH_3$. The unsaturation of the alkyl chain may have a cis or trans configuration. The preferred fatty acid primary amide is cis-9,10-octadecenoamide. Alternative preferred fatty acid primary amides include trans-9,10-octadecenoamide, cis-8,9-octadecenoamide, cis11,12-octadecenoamide, and cis-13,14-docosenoamide Preferred routes for administering the fatty acid primary amide include intraperitoneal injection (ip), subcutaneous injection (sc), intramuscular injection (im), peroral ingestion (pi), spinal injection, and cranial injection. The preferred daily dosage ranges from 1 milligram to 10 grams.

An other aspect of the invention is directed to a method for assaying a patient's level of comparative sleep deprivation. Comparative sleep deprivation is measured against a control subject. After a sample of cerebrospinal fluid is obtained from a patient, it is analyzed in order to ascertain the presence of an HPLC (high performance liquid chromatography) peak associated with fatty acid primary amides. In a preferred mode of analysis, the sample cerebrospinal fluid is chromatographically fractionated by HPLC. The peak associated with fatty acid primary amides may then be verified by mass spectrometry analysis. The patient's cerebrospinal fluid is then compared with cerebrospinal fluid obtained from a control subject, similarly analyzed, in order to determine the patient's level of comparative sleep deprivation.

Another aspect of the invention is directed to methods for isolating molecules which bind to fatty acid primary amides. The method employs the step of contacting the subject molecules with a fatty acid primary amide which is immobilized onto a solid phase substrate. Bound molecules may then be isolated by elution from the immobilized fatty acid primary amide.

DETAILED DESCRIPTION

Abbreviations: collision-induced dissociation (CID), mass spectrometry/mass spectrometry (MS/MS or $MS^2$), mass spectrometry/mass spectrometry/mass spectrometry (MS/MS/MS or $MS^3$), specific pathogen free (SPF)

Sleep Deprivation and Collection of Feline Cerebral Spinal Fluid

Four adult female specific pathogen free (SPF) cats (Liberty Laboratories, Liberty Corner, N.J.) were employed in these studies. Subjects weighed between 3.0–4.2 kg at the time of sampling. In order to establish a chronic cerebroventricular cannula, subjects were first placed under general anesthesia (halothane), intubated and restrained in a feline stereotaxic apparatus (David Kopf Inc. Tujunga Calif.). A trephine hole was then drilled in the cranial vault through followed by insertion of a stainless steal cannula (Plastic Products, Roanoke Va.) directed either toward the fourth (two cats) or the right lateral ventricle (two cats). Patency of the cannula placement was confirmed by observing spontaneous flow of clear, cerebrospinal fluid (CSF) from the external tip of the cannula, or by cerebrospinal fluid being able to be drawn from the cannula with a microliter syringe (Hamilton Co., Reno Nev.). The cannula and a fixed internal stilette was then encased and secured to the cranium by dental acrylic cement. Subjects were allowed at least two weeks recovery prior to sampling biological fluids. Subjects were group housed in a vivarium with regulated temperature and a 12 hour light/dark illumination cycle (lights on: 6:30 a.m.; Lights off: 6:30 p.m.). cerebrospinal fluid samples were extracted between the hours of 10:00 a.m. and 12:30 a.m. The cerebrospinal fluid sampling procedure involved removal of the internal stilette and inserting a small diameter cannula that extended one millimeter beyond the tip of the implanted cannula. cerebrospinal fluid was then drawn into a 100 microliter capacity Hamilton syringe and immediately placed into a small plastic container (Eppendorf microcentrifuge tube) and placed into a bucket filled with dry ice. Samples were then transferred to a −70 degree Centigrade freezer until analytical analysis. A total of six samples were collected in this fashion. Individual samples varied in volume from 150 to 300 microliters. In addition to this procedure two felines were placed on an enclosed, slowing moving treadmill for twenty-two hours thereby enforcing partial sleep deprivation. One cerebrospinal fluid sample of these subjects was taken following this period of sleep deprivation. Finally, two additional cerebrospinal fluid samples were taken from Ketamine anesthetized felines by acute transcutaneous puncture through the cistera magna.

HPLC Experiments

Preparative HPLC analysis of the cerebral spinal fluid was performed on a Pharmacia LKB Biotechnology SMART System with a MicroPeak monitor. A "μRPC C2/C18, SC 2/10" column was used to perform the separation; a flow of 100 μl/min was maintained with a 1% acetonitrile/water (0.1% TFA) gradient. The fraction collector collected the sample directly from the detector which monitored absorbance at two wavelengths, 215 and 280 nm. Direct coupling of the HPLC with the mass spectrometer was also achieved with a Michrom HPLC.

Physical Analysis

Reported herein is the isolation of a compound with the chemical formula $C_{18}H_{35}NO$ from the cerebrospinal fluid of sleep-deprived cats. Based on the synthesis and evaluation of model compounds and candidate structures, the data have also been found to be compatible with a monounsaturated alkane chain terminating in a primary amide (M. K. Jain et. al., (1992): *J. Med. Chem.*, vol. 35, page 3584. It is demonstrated herein through the use of electrospray MS, GC- MS, TLC, IR, NMR, and chemical degradation procedures that the structure of the isolated $C_{18}H_{35}NO$ is cis-9,10-octadecenoamide, illustrated as compound 1 in FIG. 7. This is also consistent with fast atom bombardment (FAB) and electrospray mass spectroscopy analysis. Related compounds in the cerebrospinal fluid of rat and man can also be detected indicating that cis-9,10-octadecenoamide is but one member of a family of fatty acid primary amides differing in the length of the alkyl chain and the position or configuration of the olefin. Importantly, we now also show that synthetic cis-9,10-octadecenoamide demonstrates sleep-inducing properties when injected into subject animals, e.g. rats.

Figure 7:
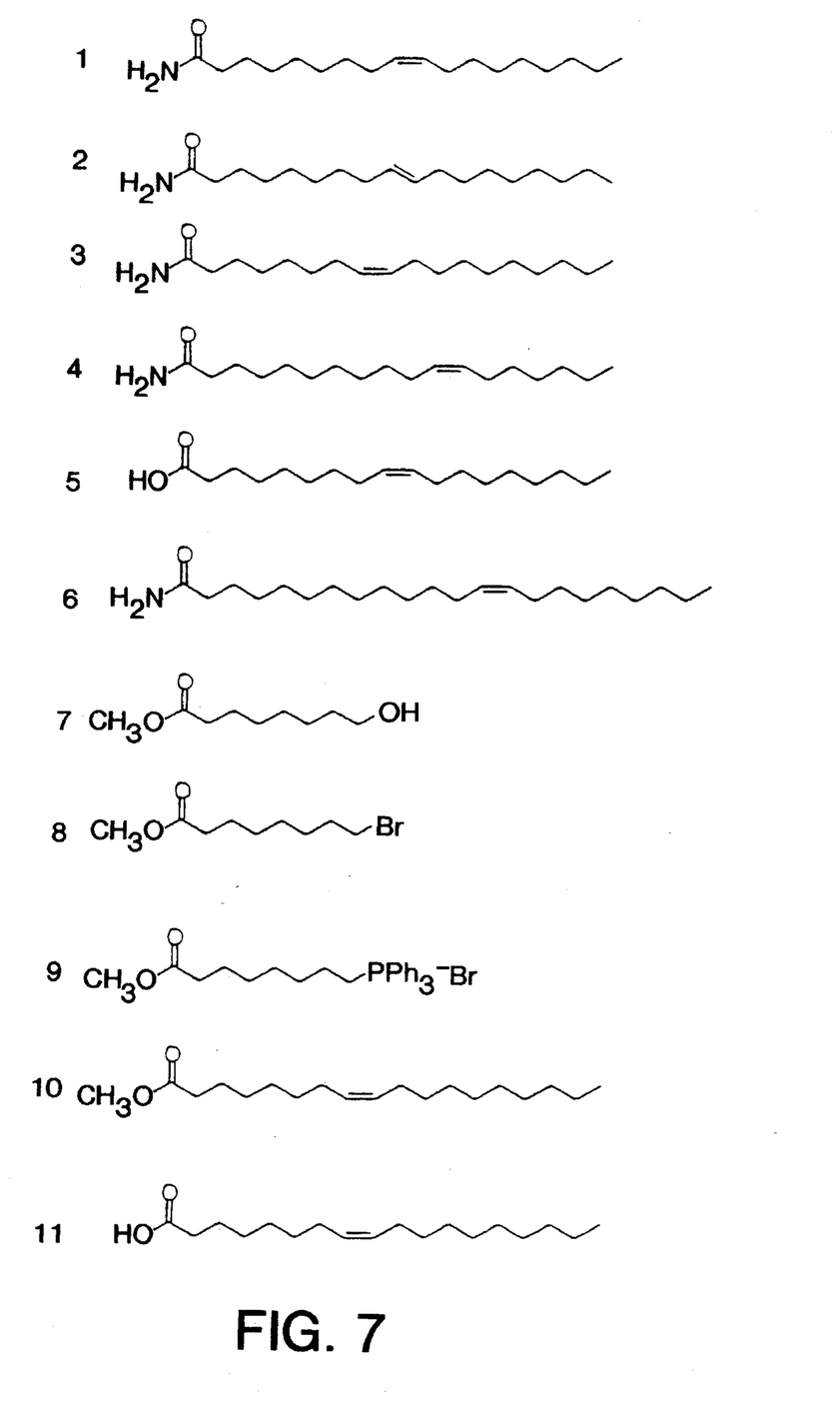
FIG. 7 illustrates the structures of natural agent, cis-9,10-octadecenoamide (1), related analogs (2–6), and compounds 7–11, precursors to 3. Compound 6 is the preferred structure for naturally occurring $C_{22}$ fatty acid amide.
Figure 8A:
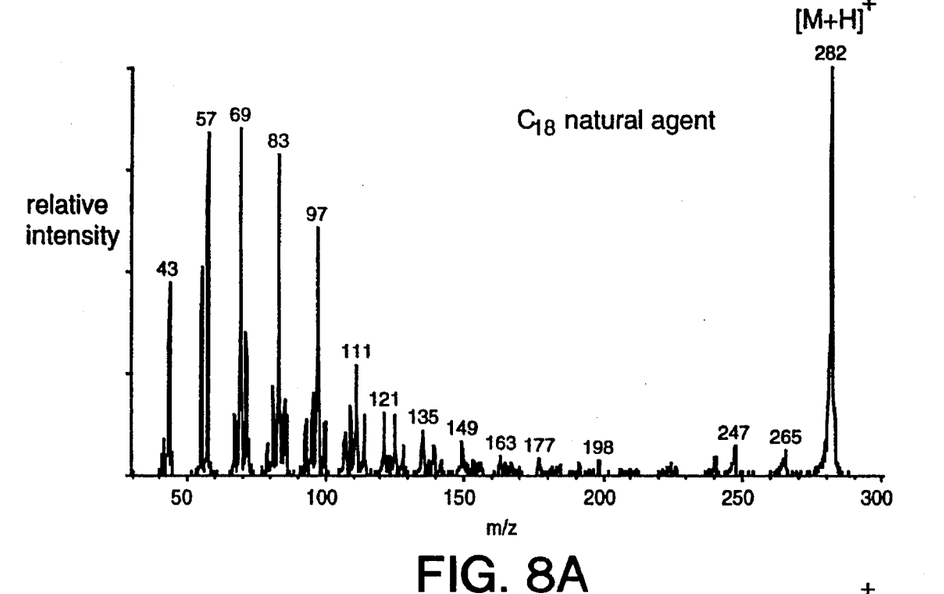
FIG. 8 illustrates tandem mass spectral data obtained for the natural compounds isolated from cerebrospinal fluid and their synthetic versions. Spectra (A) and (C) represent the fragmentation data obtained for the natural $C_{18}$ and $C_{22}$ agents, respectively. Spectra (B) and (D) represent the fragmentation data obtained for synthetic cis-9,10-octadecenoamide and cis-13,14-docosenoamide, respectively.
Figure 8B:
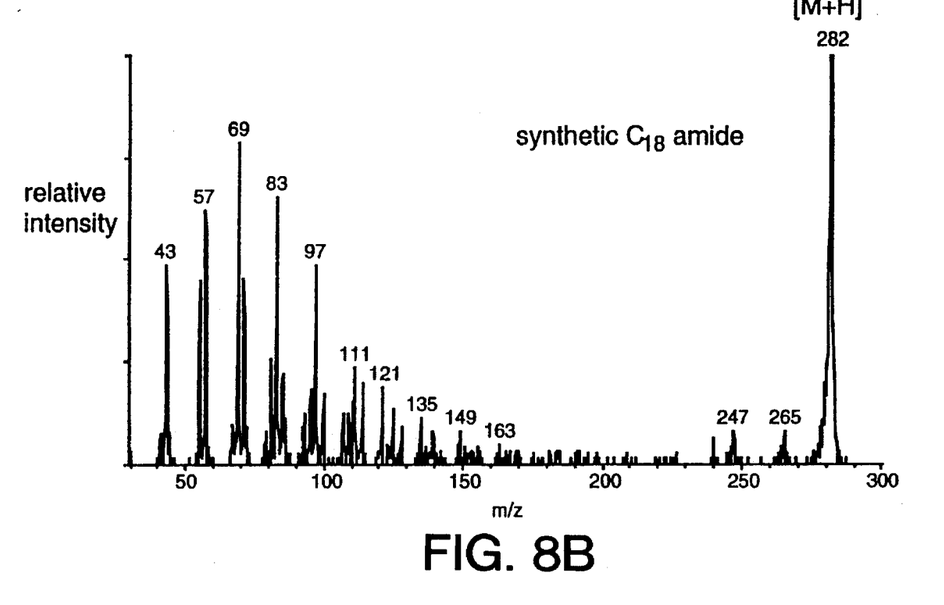
Figure 8C:
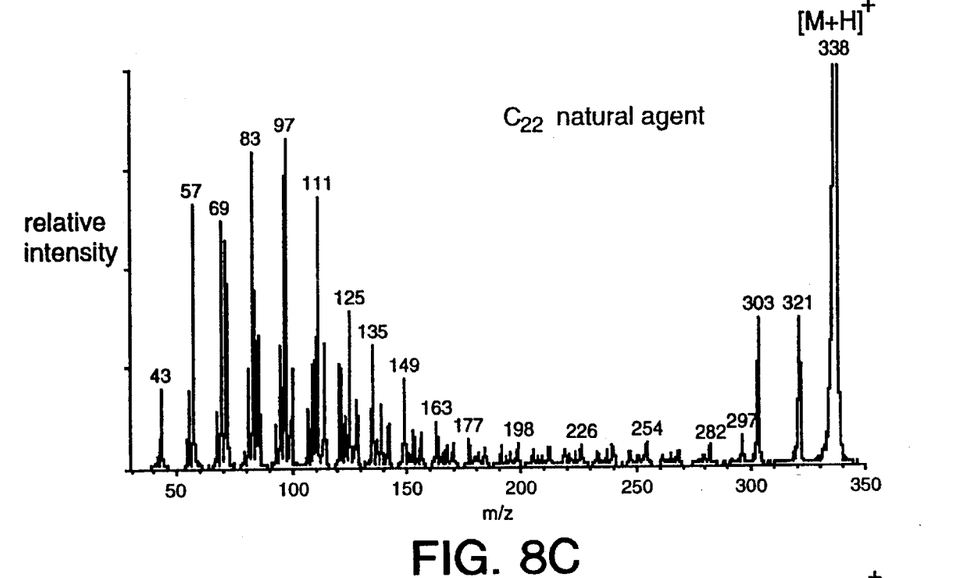
Figure 8D:
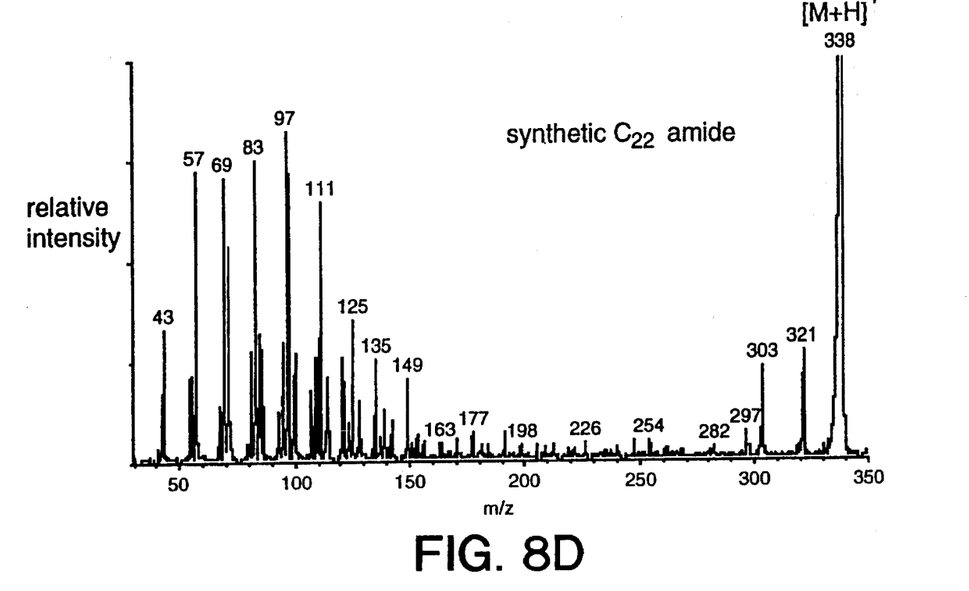

Initial electrospray mass analysis of the natural compound revealed mass peaks of m/z 282 $[M+H]^+$, 304 $[M+Na]^+$, 320 $[M+K]^+$, and 564 $[2M+H]^+$, indicating that the molecular mass of the compound was 281 Da (1). High-resolution FAB-MS analysis allowed the exact mass measurement of the $[M+Na]^+$ion, and the observed mass was m/z 304.2614±0.0006 Da. This measurement allowed for determination of elemental composition and a best fit for the molecular formula $C_{18}H_{35}NO$, which has a calculated $[M+Na]^+$ m/z of 304.2616 Da. Tandem mass analysis revealed a distinctive fragmentation pattern in the low molecular mass range consistent with other long chain alkanes (FIG. 8A). Sequential neutral loss of 17 and 35 from the parent ion indicated loss of ammonia followed by loss of water. Additional $MS^3$ experiments were performed on the daughter ions of m/z 265 and 247 (1). Such $MS^2$ and $MS^3$ mass analyses were also performed on various synthetic candidate structures. α-Amino ketones were readily distinguishable from the natural agent by fragmentation pattern analysis. $\Delta^{3,4}$-1-Hydroxy-2-aminooctadecadienes (1) exhibited nearly identical fragmentations to the natural lipid only differing in the relative intensities of lower molecular weight fragments in $MS^2$ experiments. While several products gave spectra quite similar to the spectra of the natural material, only the fragmentation patterns generated from monounsaturated fatty acid amides, like cis-9,10-octadecenoamide, as illustrated in FIG. 7B, matched exactly those of the endogenous lipid. The neutral loss of 17 mass units from the parent ion of cis-9,10-octadecenoamide indicates that the molecule first fragments at the carbon-nitrogen bond of its terminal amide group to release ammonia. Mass analysis also identified a compound from the spinal fluid of man and rat with the molecular formula $C_{22}H_{43}NO$ whose $MS^2$ and $MS^3$ fragmentation patterns were found to be indistinguishable from those of synthetic cis-13,14-docosenoamide, as illustrated in FIGS. 9C and 9D. The natural compound $C_{22}H_{43}NO$ and synthetic cis-13,14-docosenoamide also exhibited identical elution properties on TLC, and ozonolysis experiments indicate that the olefin of the $C_{22}$ natural agent is in the 13,14 position.

Cis-9,10-octadecenoamide and the $C_{18}$ natural lipid exhibited identical elution properties on TLC and GC-MS. TLC ($SiO_2$) provided an $R_f$ of 0.3 with 75% ethyl acetate/ hexanes. GC-MS analyses were carried out on a 5890 Hewlett Packard GC with a 5971A Hewlett Packard mass selective detector. Separations were performed on a DB-5 (0.25 mm film) capillary column that was 30 m in length and had an internal diameter of 0.25 mm. The column temperature was programmed to increase from 50° C. to 290° C. at a rate of 20° C. per minute. The column was maintained at the final temperature of 290° C. for an additional 10 minute. The injector temperature was 250° C. and the detector temperature was 290° C. The compounds were injected into the GC in $CH_2Cl_2$. The electron energy in EI measurements was 70 eV with one scan per second. Retention times: synthetic cis-9,10-octadecenoamide, 16.95 minute; natural compound, 16.96 minute.

However, these analytical techniques proved insensitive to the position and configuration of the double bond of closely related synthetic fatty acid amides, and the cis-8,9 (3), cis-9,10 (1), cis-11,12 (4), and trans-9,10 (2) octadecenoamides were not distinguishable from the natural compound by TLC and GC.

Cis-9,10-octadecenoamide, cis-11,12-octadecenoamide, and trans-9,10-octadecenoamide were prepared from their respective acids as follows: cis-9,10-octadecenoic acid (oleic acid) in $CH_2Cl_2$ (0.2M) at 0° C. was treated with oxalyl chloride (3 eq) and stirred at 25° for 4 hour. Removal of solvent followed by treatment with saturated aqueous $NH_4OH$ at 0° C. gave cis-9,10-octadecenoamide, which was purified by silica gel column chromatography (40–75% ethyl acetate-hexanes gradient elution). Cis-8,9-octadecenoamide was synthesized as follows: 1) Suberic acid monomethyl ester in THF at −20° C. was treated with $BH_3$-THF (1.05 eq) and stirred for 12 hour at 25° C. to afford methyl 8-hydroxyoctanoate (18); 2) Methyl 8-hydroxyoctanoate in $CH_2Cl_2$ at 0° C. was treated sequentially with $CBr_4$ (1.3 eq) and $Ph_3P$ (1.4 eq) and stirred for 10 hour at 4° C. to give methyl 8-bromooctanoate; 3) Methyl 8-bromooctanoate was dissolved in $CH_3CN$ (0.8M) and warmed at reflux. $Ph_3P$ (1.1 eq) was added to the solution and stirring was continued for 20 hour to afford the corresponding phosphonium salt; 4) The phosphonium salt of methyl 8-bromooctanoate was dissolved in THF at 25° C. and treated with KHMDS (1.1 eq). After stirring at reflux for 1 hour, the solution was cooled to −78° C. and decanal (1.5 eq) was added. The mixture was allowed to warm to 25° C. and stirred for 30 minute to afford methyl cis-8,9-octadecenoate; 5) Methyl cis-8,9-octadecenoate was hydrolyzed to afford cis-8,9-octadecenoic acid with LiOH (3 eq) in THF-$CH_3OH$—$H_2O$ (3:1:1); 6) Conversion of cis-8,9-octadecenoic acid to cis-8,9-octadecenoamide was conducted as described above.

Through IR, NMR, and chemical degradation procedures, the exact structure of the endogenous lipid, including the position and configuration of its olefin was unambiguously determined. The position of the double bond along the alkyl chain of the natural compound was determined by chemical degradation. (O. S. Privett, *Progress in the Chemistry of Fats and Other Lipids* (1966): vol. 9, page 91). Chemical degradation techniques were employed first on synthetic fatty acid amides, identifying ozonolysis as conducive to the analysis of these agents. Ozonolysis of the natural agent was carried out as follows: approximately 100 mg of the natural lipid was dissolved in $CH_2Cl_2$ (300 milliliter) and cooled to −78° C. 600 milliliter of ozone saturated $CH_2Cl_2$ (generated at −78° C.) was added to the mixture and stirring was continued at −78° C. for 30 minute. Excess ozone was removed by purging the reaction mixture with argon, and the ozonide products were reduced with the addition of dimethylsulfide (excess). The reaction mixture was warmed to 0° C. and stirred for 1 hour, and 25° C. for 1 hour. The solvent was evaporated and the residue was redissolved in 50 milliliter of diethyl ether and directly analyzed by GC/MS.

GC-MS analysis of the ozonolysis reaction mixture derived from the natural lipid revealed nonyl aldehyde as the only C-terminal aldehyde present. GC/MS analyses were carried out as described supra. The GC program used to analyze the aldehyde product(s): after 4 minute at an initial temperature of 50° C., the column temperature was increased at a rate of 10° C. per minute until a final temperature of 200° C. was reached. The column temperature was maintained at 200° C. for an additional 5 minute. Retention times: nonyl aldehyde, 10.78 minute; ozonolysis reaction of natural compound, 10.76 minute. Nonyl aldehyde corresponds to an olefin positioned seven methylenes removed from the terminal methyl group of the alkyl chain, which in the case of a $C_{18}$ fatty acid primary amide, is the 9,10 position.

The IR spectrum of the natural compound (neat) exhibited absorbances at 3354 and 3320 (amide N—H stretches), 2923 and 2851 (alkane stretches), 1656 and 1630 (amide I and II bands), 1466, and 1410 cm$^{-1}$. While cis-9,10-octadecenoamide gave an FTIR spectrum identical to that of the natural agent, a single characteristic difference was observed in the IR spectra of the endogenous lipid and trans-9,10-octadecenoamide, as only the trans isomer exhibited a strong absorption peak at 960 cm$^{-1}$. Neither the natural compound nor cis-9,10-octadecenoamide exhibited this IR absorption band characteristic of disubstituted trans alkenes. (W. W. Christie, *Lipid Analysis*, Pergamon Press, Oxford, 1973, pp. 128.)

Through extensive isolation efforts, we were ultimately able to secure approximately 300 mg of the endogenous lipid, which proved a sufficient quantity to acquire proton NMR data on the compound. After HPLC isolation of the natural compound as described previously, the HPLC fractions were combined, concentrated, and resuspended in the minimum volume of $CH_2Cl_2$. Silica gel chromatography (40–75 % ethyl acetate/hexanes) of the crude product afforded approximately 300 mg of the natural compound. Residual impurities including grease at d 1.2 account for the variation in the $^1$H NMR peak intensities in this region when compared to synthetic cis-9,10-octadecenoamide. The $^1$H NMR spectrum ($CD_3OD$, 400 MHz) exhibited the following peaks: d 5.24 (multiplet, 2H, olefinic protons), 2.09 (triplet, 2H, $H_2NC(O)CH_2$), 1.93 (multiplet, 4H, allylic protons), 1.50 (multiplet, 2H, $H_2NC(O)CH_2CH_2$), 1.50–1.23 (multiplet, alkyl methylene protons), and 0.805 (triplet, 3H, $CH_3$). When compared to the $^1$H NMR spectra of trans- and cis-9,10-octadecenoamide, the natural compound and cis-9,10-octadecenoamide were identical and definitively different from trans-9,10-octadecenoamide. Samples of the natural lipid and cis-9,10-octadecenoamide were distinguishable from the trans isomer in both the olefinic and allylic regions of the $^1$H NMR spectrum. Whereas the olefinic protons of the trans isomer reside at d 5.28 in $CD_3OD$, the olefinic protons of the natural compound and the cis isomer are shifted slightly upfield to d 5.24. In the allylic region of the NMR spectrum, both the natural compound and the synthetic cis isomer have a four proton peak ranging from d 1.94 to 1.91, while the allylic protons of the trans isomer are observed at d 1.88 to 1.86. Trace amounts of the trans fatty acid amide do appear to be present as well in the natural sample, indicating perhaps that this agent is also an endogenous constituent of the brain. Most trans fatty acids in tissue lipids from non-ruminant organisms probably originate solely from dietary sources (R. P. Mensink and M. B. Katan, *Prog. Lipid Res.* 32, 111 (1993)). Evidence suggests that these exogenous trans fatty acids are metabolized normally, and the identification of trans-9,10-octadecenoamide from cerebrospinal fluid may indicate natural conversion of dietary elaidic acid into its amide derivative. Elaidic acid has been identified as a trace constituent of human brain lipids (R. O. Adlof and E. A. Emken, *Lipids* 21, 543 (1986)). Alternatively, slight isomerization during the isolation procedures could account for the presence of the small amounts of the trans isomer. Thus, through the use of MS, GC, TLC, IR, NMR, and ozonolysis the structure of the unknown natural lipid was determined to be cis-9,10-octadecenoamide.

Mass Spectrometry

The mass spectrometry experiments were performed on an API III Perkin Elmer SCIEX triple-quadrupole mass spectrometer and a Fisons/VG ZAB-VSE high resolution magnetic sector mass spectrometer. The pneumatically-assisted electrospray interface on the SCIEX was used for sample introduction with the potential of the interface sprayer maintained at 5.0 kV. A curtain gas of ultra pure nitrogen (1.0 liters/minute) between the interface plate and the sampling orifice was applied to aid desolvation of the charged droplets and to prevent particulate matter from entering the analyzer region. Samples were introduced through the interface at a rate of 4.0 ml/minute. The positive ions generated by the ion evaporation process entered the analyzer through an interface plate and a 100 mm orifice. The declustering potential was maintained between 50–250 V (typically 100 V) to control the collisional energy of the entering ions. A cryogenic pump was used to cool the surfaces within the spectrometer (14–18K) maintaining a working pressure of $2\times10^{-5}$ Torr and a sealed pressure of $8\times10^{-8}$ Torr of in the analyzer region. The Fisons/VG ZAB-VSE instrument was used to perform the exact mass determination on the unknown compound by fast atom bombardment (FAB) analysis; a resolution of 10,000 (10% valley definition) was obtained to perform an exact mass measurement to within 0.7 parts per million.

Collision-Induced Dissociation (CID)

The CID experiments were performed on the API III Perkin Elmer SCIEX triple-quadrupole mass spectrometer with ultra pure argon (>99.99% purity) as a collision gas. The positive ion MS/MS data were acquired by mass selecting the precursor ion with the first quadrupole, collisions with argon (target thickness of $3\times10^{14}$ atom/cm$^2$) in the second quadrupole produced dissociation. The third quadrupole mass-analyzed the resultant daughter ions. Collision energies of 80 eV were maintained in these experiments. CID spectra shown were the result of averaging from 50 to 100 scans depending on the number of scans necessary to obtain a signal to noise greater than or equal to 50. MS/MS/MS (MS$^3$) data were also obtained by mass selecting a daughter ion generated at the orifice with the first quadrupole mass analyzer. Collisions with argon (target thickness of $3\times10^{14}$ atom/cm$^2$) in the second quadrupole collision cell produced further dissociation and the resultant granddaughter ions were analyzed with the third quadrupole mass analyzer.

Results

The HPLC analysis of the feline's cerebral spinal fluid produced a peak which was present in sleep deprived but not normal cats. Its identity was determined by physical characterization, including mass spectrometry methods.

Figure 1:
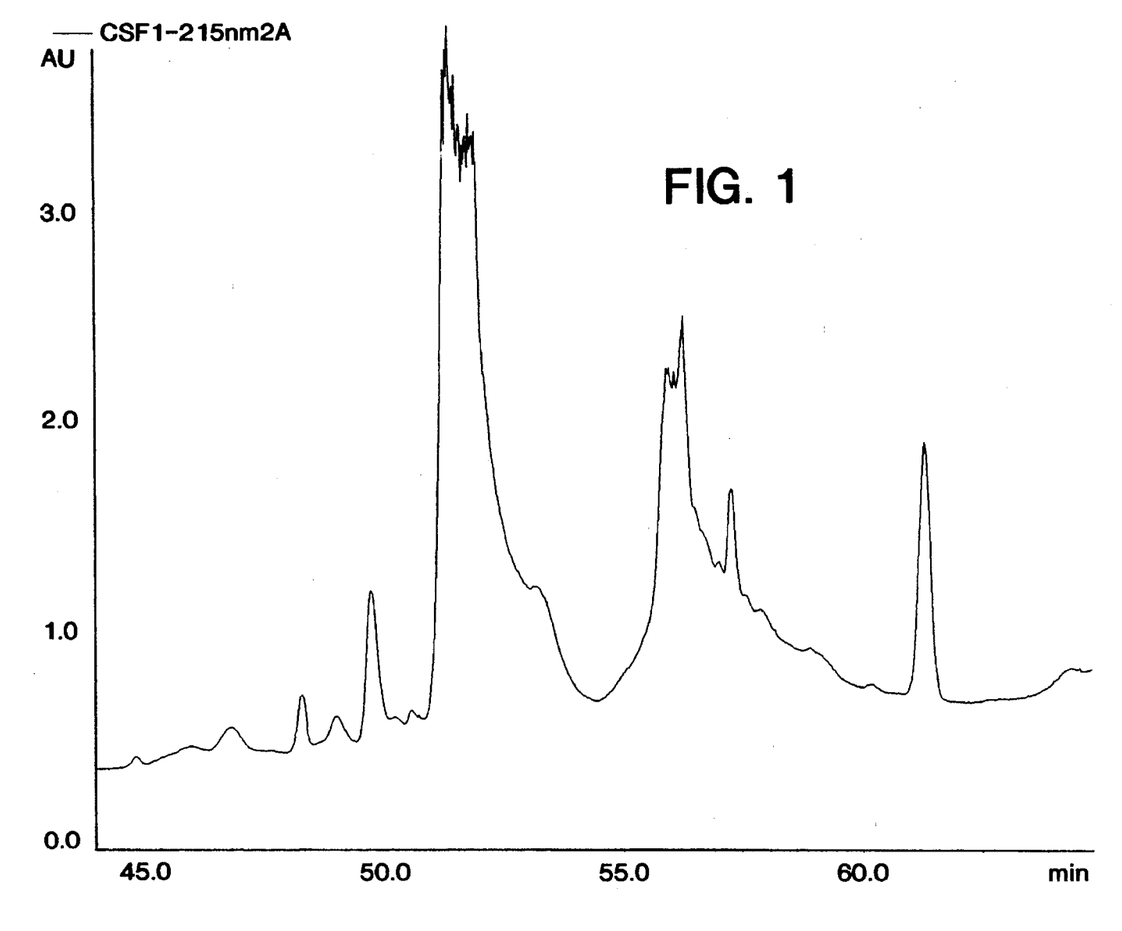
FIG. 1 illustrates an HPLC fractionation of cerebrospinal fluid obtained from a control subject. HPLC analysis spinal fluid was performed on a Pharmacia LKB Biotechnology SMART System with a MicroPeak monitor. A "μRPC C2/C18, SC 2/10" column was used to perform the separation; a flow of 100 μl/min was maintained with a 1% acetonitrile/water (0.1% TFA) gradient. The fraction collector collected the sample directly from the detector which monitored absorbance at two wavelengths, 215 and 280 nm.
Figure 2:
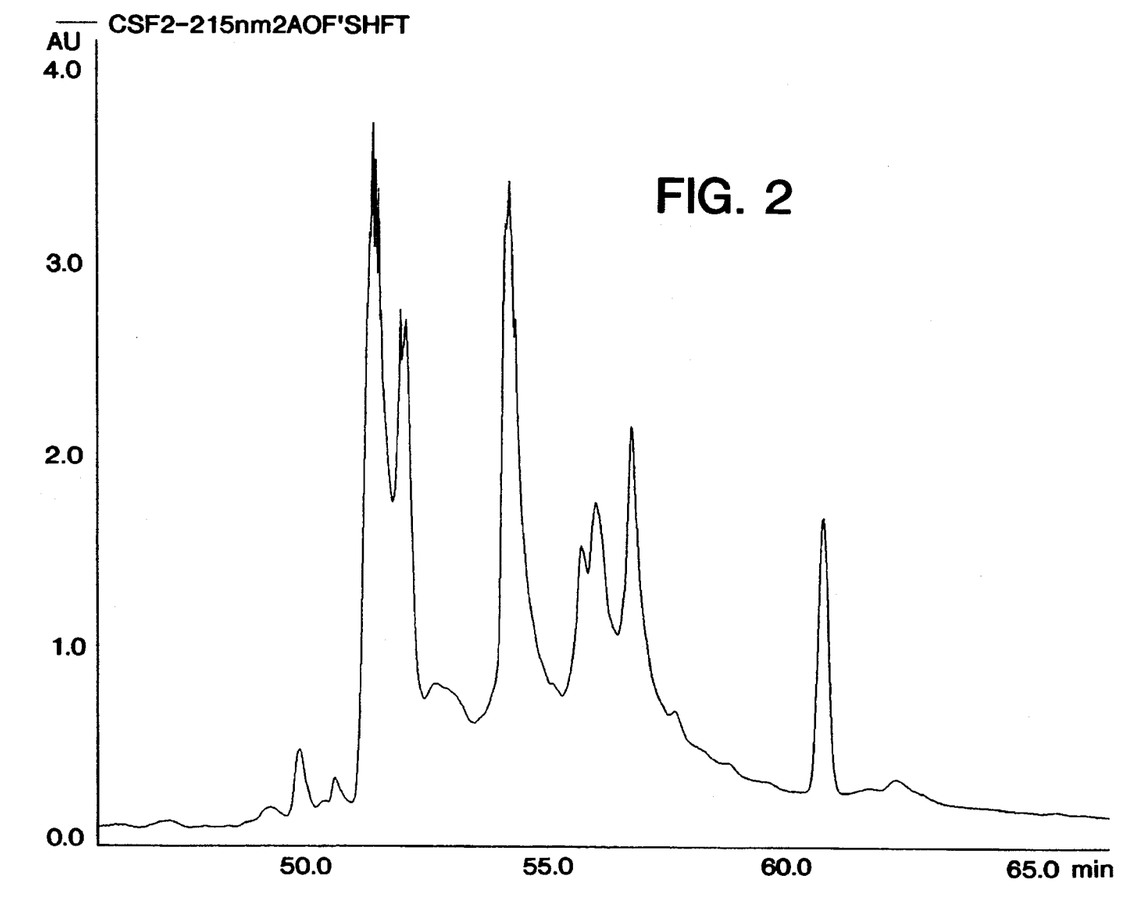
FIG. 2 illustrates an HPLC fractionation of cerebrospinal fluid obtained from a sleep deprived subject. Analysis of the HPLC fractions discloses that the major new peak occurring at 54 minutes is correlated with the presence of cis-9,10-octadecenoamide.
Figure 3:
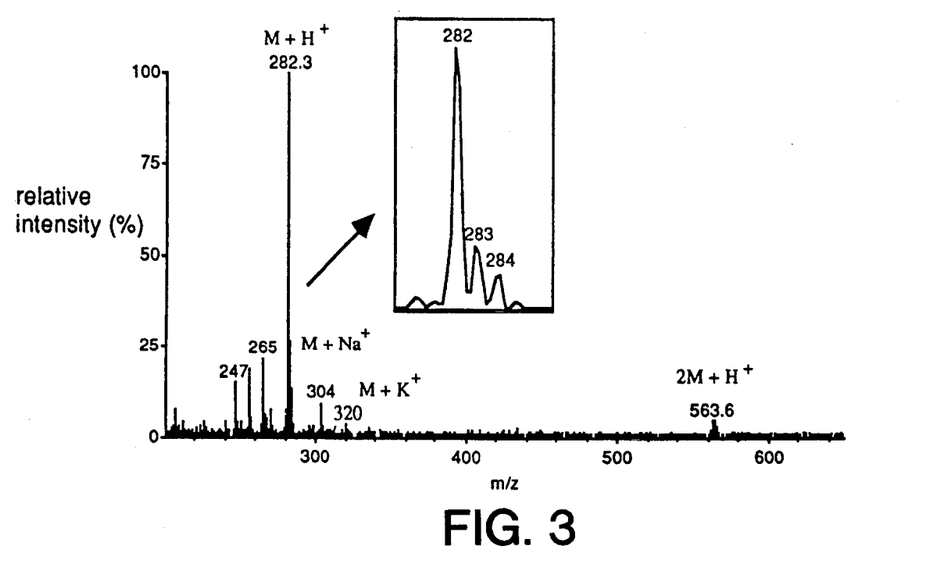
FIG. 3 illustrates a mass spectrum of the compound obtained from the fraction corresponding to the peak shown in FIG. 2. The observation of the noncovalent dimer and the $Na^+$ ($[M+Na^+]^+=304$ Da) and $K^+$ ($[M+K^+]^+=320$ Da) adducts confirm that the observed mass ($[M+H^+]^+=282$ Da) compound in question is not a fragment of a larger compound.

Initial electrospray mass analysis of this peak revealed a m/z=282, 304, 320, and 564, FIG. 3. The observation of these peaks $[M+H^+]^+$(m/z=282), $[M+Na^+]^+$(m/z=304), $[M+K^+]^+$(m/z=320), and $[2M+H^+]^+$(m/z=564), were an indication that the molecular weight of the compound was 281 Da. The cation adducts and the noncovalent dimer suggest that the ion is not a fragment of a higher molecular weight compound.

In addition, analysis of the isotope pattern of the 282 $[M+H^+]^+$ peak (FIG. 3) revealed isotopes separated by one mass unit, thus eliminating the possibility that this was a multiply charged ion corresponding to a higher molecular weight compound. High resolution analysis by fast atom bombardment mass spectrometry allowed for the exact mass measurement of the $[M+Na^+]^+$ ion, observed mass= 304.2614±0.0006 Da. This measurement allowed for determination of elemental composition and a best fit for the molecular formula, $C_{18}H_{35}NO$, calculated $[M+Na^+]^+$ mass= 304.2616 Da. A strong protonated signal indicated that the compound had a high proton affinity even in the presence of $Na^+$, suggesting the compound is an amine. Tandem mass analysis was performed in order to gain structural information on this compound.

Figure 4:
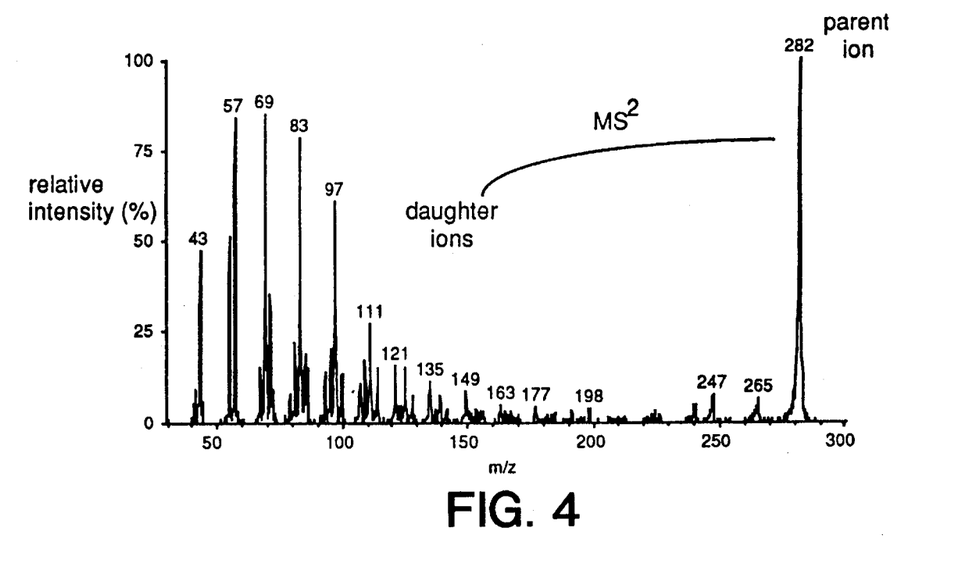
FIG. 4 illustrates the $MS^2$ data on the parent ion, m/z=282.
Figure 5:
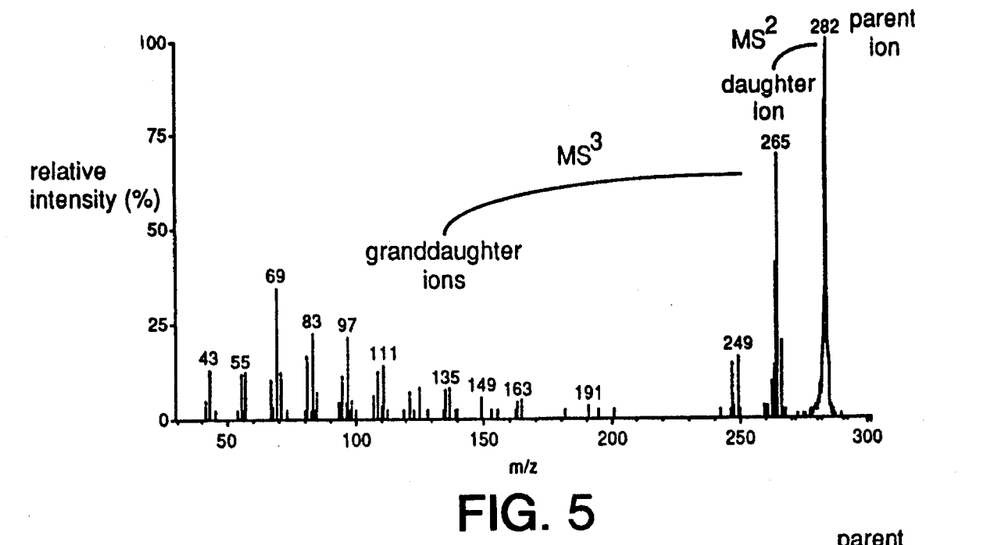
FIG. 5 illustrates the $MS^3$ data on the daughter ion 265. The parent ion, 282, is added to the spectrum for clarity.
Figure 6:
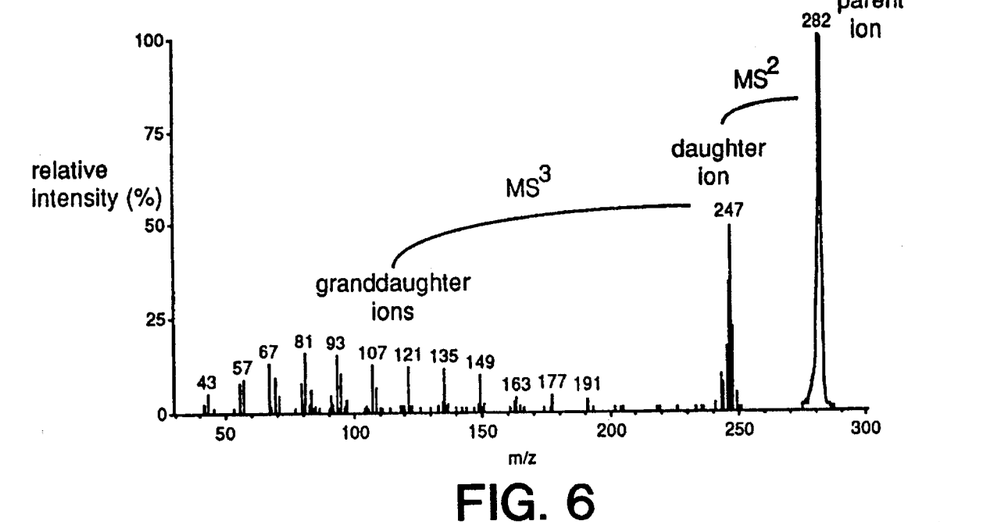
FIG. 6 illustrates the $MS^3$ data on the daughter ion 247. The parent ion, 282, is added to the spectrum for clarity.

Tandem mass analysis (FIG. 4) of this fraction revealed a distinctive fragmentation pattern in the low molecular mass range consistent with other long chain alkanes. Neutral losses of 17 and 35 from the parent ion indicated a loss of ammonia followed by water. Additional $MS^3$ experiments were performed on the daughter ions 265 and 247. The $MS^3$ experiments (FIG. 6) revealed that the 265 daughter ion fragments to form the 247 granddaughter ion. This suggests that the 247 is the result of sequential losses (loss of 17 $\{-NH_3\}$ followed by 18 $\{-H_2O\}$) as opposed to a neutral loss independent of the 265 daughter ion.

The 249 ion generated in the $MS^3$ spectrum of the 265 ion was determined to be from another component in the HPLC fraction. The CID analysis of a 281 ion revealed loss of 16 and 32 to produce the ions 265 and 249, respectively. The 249 ion is probably the granddaughter ion from the parent ion, m/z=281, produced from the daughter ion at m/z=265.

The data collected on cis-9,10-octadecenoamide are partially summarized in Table I.

TABLE I

| DATA TYPE | SUMMARY OF DATA |
| --- | --- |
| EXACT MASS | $[C_{18}H_{35}N_1O_1 + Na^+]^+$ observed 304.2614 expected 304.2616 |
| $D_2O$ MS | m/z = 286 = $[M - 3H^+ + 4D^+]^+$ indicates 3 exchangeable protons. |
| ISOTOPE | isotope pattern at m/z = 282 indicates that 282 is not a multiply charged species, nor does it have any elements with an unusual isotope pattern (e.g. Cl or Br). |
| CATIONIZATION | Electrospray MS observation of 304 $[M + Na^+]^+$ and 320 $[M + K^+]^+$ confirms that M = 281 Da fast-atom bombardment and electrospray MS of compound in the presence of $Na^+$ showed relatively weak formation of $[M + Na]^+$ with strong formation of $[M + H]^+$. |
| ASSOCIATION | 563.6 association product $[2M + H^+]^+$ further confirmation that M = 281 Da. |
| $MS^2$ DATA | fragment ion 265 may correspond to $[MH^+ - NH_3]^+$ fragment ion 247 may correspond to $[MH^+ - NH_3 - H_2O]^+$. lipid fragments. |
| $MS^3$ DATA | Fragmentation of 265 >> 247 (sequential loss), suggests 247 fragment is related to 265 fragment ion. lipid fragmentation pattern. |
| UV | 215 absorbance. |
| NMR | confirms lipid portion to molecule and unconjugated diene structure. |

Protocols for the Induction of Sleep

Synthetic cis-9,10-octadecenoamide was injected (ip) into rats in order to test its effect on spontaneous behavior at different doses: 1 (n=2), 2 (n=2), 5 (n=7), 10 (n=10), 20 (n=2), and 50 (n=2) mg, where n=number of rats tested. Rats were injected during a reversed dark period (12:12) two hours after the lights cycled off and were observed in their home cages. With the lower doses (1 and 2 mg), no overt effect on spontaneous behavior was witnessed. However, at a threshold of 5 mg and above there was a marked effect consisting of an induction of long-lasting motor quiescence associated with eyes closed, sedated behavior characteristic of normal sleep. Also as with normal sleep, the rats still responded to auditory stimuli with orienting reflex and sustained attention toward the source of stimulation. In addition, motor behavior was impaired. The latency to behavioral sedation following administration was about 4 minutes and subjects were normally active again after 1 hour (5 mg), 2 hour (10 mg), or 2.5 hour (20 mg and 50 mg).

We have compared cis-9,10-octadecenoamide to vehicle and the synthetic analogs listed in FIG. 7 to estimate the structural specificity of its sleep-inducing potential. Neither vehicle (5% ethanol in saline solution) nor oleic acid (5) showed any overt behavioral effect. Trans-9,10-octadecenoamide demonstrated similar pharmacological effects to its cis counterpart, but was much less potent as measured by the comparatively shorter duration time for its sleep-inducing properties (at 10 mg per rat, the biological effect lasted one hour for the trans isomer and two hours for the cis isomer). When the olefin was moved either direction along the alkyl chain (to the 8,9 (3) or 11,12 (4) positions) or the alkyl chain length was extended to 22 carbons (6), a substantial reduction in both the degree and duration of the pharmacological effects was observed, and while the mobility of the rats still decreased, their eyes remained open and their alertness appeared only slightly affected. Finally, polysomnographic studies on rats injected with cis-9,10-octadecenoamide show an increase in the total time of slow wave sleep (SWS) as well as in the mean duration of the SWS individual periods when compared to vehicle controls. More particularly, male Sprague-Dawley rats (300 g at the time of surgery) were implanted under halothane anesthesia (2–3%) with a standard set of electrodes for sleep recordings. This included two screw electrodes placed in the parietal bone over the hippocampus to record the subjects electroencephalogram (EEG) and two wire electrodes inserted in the neck musculature to record postural tone through electromyographic activity (EMG). Rats were housed individually with at libitum access to food and water. The dark-light cycle was controlled (12:12, lights on a 10:00 p.m.). One week after the surgery, rats were habituated to the recording conditions for at least three days. Upon the completion of the habituation period, rats received 2 milliliter (ip) of either: vehicle (5% ethanol/saline solution), cis-9,10-octadecenoamide (10 mg), or oleic acid (10 mg). Rats were continuously recorded for four hours after the ip injection (12:00 p.m.–4:00 p.m.) Rats were observed for spontaneous changes in behavior through a one-way window. Sleep recordings were visually scored and four stages were determined: wakefulness, slow-wave-sleep 1 (SWS1), slow-wave-sleep 2 (SWS2), and rapid eye movement (REM) sleep.

These increases with respect to slow wave sleep (SWS) were at the expense of waking. Distribution of REM sleep does not seem to be altered. Together, these data suggest that cis-9,10-octadecenoamide could play an important role in slow-wave sleep modulation.

The traditional view of lipid molecules as passive structural elements of cellular architecture is rapidly giving way to an ever increasing awareness of the active roles these agents play in transducing cell signals and modifying cell behavior, e.g., M. Liscovitch and L. C. Cantley, *Cell* (1994):

vol. 77, page 329. An intriguing feature of the fatty acid amides studied here is that they belong to a family of simple molecules in which a great deal of diversity may be generated by simply varying the length of the alkane chain and the position, stereochemistry, and number of its olefin(s). Interestingly, other neuroactive signalling molecules with amide modifications at their carboxy termini have been reported, from carboxamide terminal peptides to arachidonylethanolamide. Neuroactive signalling molecules employing carboxamide terminal peptides are disclosed by B. A. Eipper, D. A. Stoffers, and R. E. Mains in *Annu. Rev. Neurosci.* (1992): vol. 15, page 57. Neuroactive signalling molecules employing arachidonylethanolamide is disclosed by W. A. Devane, L. Hanus, A. Breuer, R. G. Pertwee, L. A. Stevenson, G. Griffin, D. Gibson, A. Mandelbaum, A. Etinger, and R. Mechoulam in *Science* (1992): vol. 258, page 1946. It is disclosed herein that cis-9,10-octadecenoamide is a member of a new class of biological effectors in which simple variations of a core chemical structure have unique physiological consequences.

Production of Immobilized Fatty Acid Primary Amides

Immobilized fatty acid primary amides may be fabricated using the 18-hemisuccinate-cis-9,10-octadecenoamide (12), whose synthesis is provided infra. The 18-hemisuccinates may then be coupled to solid phase affinity chromatography matrix material employing conventional materials and protocols as provided, for example, by Sigma kits. The immobilized fatty acid primary amide may then be employed for binding molecules having an affinity therewith and for isolating such molecules by elution.

Synthesis of Fatty Acid Primary Amides

Preferred protocols for synthesizing exemplary fatty acid primary amides are provided. The synthetic protocols differ only with respect to the chain length of the starting materials, the product yields, and the separation of the various cis and trans products. Accordingly, exemplary descriptions of synthetic protocols for the synthesis of cis-9,10-octadecenoamide and several other fatty acid primary amides are provided and serve to illustrate the synthetic protocol for the entire class of fatty acid primary amides.

Synthetic Methods

Cis-9,10-octadecenoamide (1). A solution of oleic acid (1.0 g, 3.55 mmol, 1.0 equiv.) in $CH_2Cl_2$ (8.9 mL, 0.4M) at 0° C. was treated dropwise with oxalyl chloride (5.32 mL, 2.0M solution in $CH_2Cl_2$, 10.64 mmol, 3.0 equiv.). The reaction mixture was stirred at 25° C. for 4 h, concentrated under reduced pressure, cooled to 0° C., and treated with saturated aqueous $NH_4OH$ (2.0 mL). The reaction mixture was then partitioned between ethyl acetate (EtOAc) (100 mL) and $H_2O$ (100 mL), and the organic layer was dried ($Na_2SO_4$) and concentrated under reduced pressure. Chromatography ($SiO_2$, 5 cm×15 cm, 40–100% EtOAc-hexanes gradient elution) afforded 1 as a white solid (0.810 g, 0.996 g theoretical, 81.3%): $^1$H NMR ($CDCl_3$, 250 MHz) $\delta$6.06 (bs, 1H, $NH_2C(O)$), 5.58 (bs, 1H, $NH_2C(O)$), 5.32 (m, 2H, CH=CH), 2.16 (t, 2H, J=7.5 Hz, $CH_2C(O)NH_2$), 2.02 (m, 4H, $CH_2CH=CHCH_2$), 1.61 (m, 2H, $CH_2CH_2C(O)NH_2$), 1.29 (b s, 14H, alkyl protons), 0.87 (t, 3H, $CH_3$); FABHRMS (NBA/NaI m/e 282.2804 ($C_{18}H_{35}NO+H^+$ requires 282.2797). The regions of the spectra that distinguish between the cis and trans isomers are the olefinic protons from $\delta$5.3 to 5.2 and allylic protons from $\delta$2.0 to 1.8. These regions identify the natural compound as cis-9,10-octadecenoamide.

trans-9,10-octadecenoamide (2). A solution of elaidic acid (1.0 g, 3.55 mmol, 1.0 equiv.) in $CH_2Cl_2$ (8.9 mL, 0.4M) at 0° C. was treated dropwise with oxalyl chloride (5.32 mL, 2.0M solution in $CH_2Cl_2$, 10.64 mmol, 3.0 equiv.). The reaction mixture was stirred at 25° C. for 4 h, concentrated under reduced pressure, cooled to 0° C., and treated with saturated aqueous $NH_4OH$ (2.0 mL). The reaction mixture was then partitioned between ethyl acetate (EtOAc) (100 mL) and $H_2O$ (100 mL), and the organic layer was dried ($Na_2SO_4$) and concentrated under reduced pressure. Chromatography ($SiO_2$, 5 cm×15 cm, 40–100% EtOAc-hexanes gradient elution) afforded 2 as a white solid. The regions of the spectra that distinguish between the cis and trans isomers are the olefinic protons from $\delta$5.3 to 5.2 and allylic protons from $\delta$2.0 to 1.8. These regions identify the compound as trans-9,10-octadecenoamide.

cis-8,9-octadecenoamide (3). A solution of 11 (0.130 g, 0.461 mmol, 1.0 equiv.) in $CH_2Cl_2$ (1.5 mL, 0.31M) at 0° C. was treated dropwise with oxalyl chloride (0.69 mL, 2.0M solution in $CH_2Cl_2$, 1.38 mmol, 3.0 equiv.). The reaction mixture was stirred at 25° C. for 4 h, concentrated under reduced pressure, cooled to 0° C., and treated with saturated aqueous $NH_4OH$ (2.0 mL). The reaction mixture was then partitioned between ethyl acetate (EtOAc) (100 mL) and $H_2O$ (100 mL), and the organic layer was dried ($Na_2SO_4$) and concentrated under reduced pressure. Chromatography ($SiO_2$, 5 cm×15 cm, 40–100% EtOAc-hexanes gradient elution) afforded 3 as a white solid. (0.105 g, 0.130 theoretical, 80.8%): $^1$H NMR ($CDCl_3$, 250 MHz) $\delta$5.70–5.34 (m, 4H, $H_2NC(O)$ and CH=CH), 2.21 (t, 2H, J=7.5 Hz, $CH_2C(O)NH_2$), 2.00 (m, 4H, $CH_2CH=CHCH_2$), 1.63 (m, 2H, $CH_2CH_2C(O)NH_2$), 1.47–1.23 (m, 20H, alkyl protons), 0.87 (t, 3H, $RCH_3$); FABHRMS (NBA/CSI m/e 414.1762 ($C_{18}H_{35}NO+Cs^+$ requires 414.1773).

cis-11,12-octadecenoamide (4). A solution of $\Delta$11,12 octadecenoic acid (1.0 g, 3.55 mmol, 1.0 equiv.) in $CH_2Cl_2$ (8.9 mL, 0.4M) at 0° C. was treated dropwise with oxalyl chloride (5.32 mL, 2.0M solution in $CH_2Cl_2$, 10.64 mmol, 3.0 equiv.). The reaction mixture was stirred at 25° C. for 4 h, concentrated under reduced pressure, cooled to 0° C., and treated with saturated aqueous $NH_4OH$ (2.0 mL). The reaction mixture was then partitioned between ethyl acetate (EtOAc) (100 mL) and $H_2O$ (100 mL), and the organic layer was dried ($Na_2SO_4$) and concentrated under reduced pressure. Chromatography ($SiO_2$, 5 cm×15 cm, 40–100% EtOAc-hexanes gradient elution) afforded 4 as a white solid.

oleic acid (5). Aldrich chemical company CAS #112-80-1.

erucamide (6). Aldrich chemical company CAS #28,057-7.

methyl-8-hydroxy-octanoate (7). A solution of suberic acid monomethyl ester (15 g, 7.97 mmol, 1.0 equiv.) in tetrahydrofuran (THF) (32.0 mL, 0.25M) at –20° C. was treated Scheme 1 dropwise with BH₃.THF (1M solution in THF, 7.97 mL, 7.97 mmol, 1.0 equiv.). The reaction mixture was stirred overnight and was subsequently allowed to reach room temperature. The reaction mixture was then diluted with ethyl acetate (100 mL) and quenched with methanol (10 mL) and 10% HCl (10 mL). Extraction with NaHCO₃ (1×20 mL), water (2×10 mL), and brine (1×10 mL), afforded methyl-8-hydroxy-octanoate (7) as a crude white solid.

methyl-8-bromo-octanoate (8). A solution of crude methyl-8-hydroxy-octanoate (7, 1.24 g, 7.13 mmol, 1.0 equiv.) in CH₂Cl₂ (15 mL, 0.48M) at 0° C. was treated successively with CBr₄ (3.07 g, 9.27 mmol, 1.3 equiv.) and PPh₃ (2.61 g, 9.98 mmol, 1.4 equiv.) and the reaction mixture was stirred at 4° C. for 10 h. The, reaction mixture was then concentrated under reduced pressure and washed repeatedly with Et₂O (8×10 mL washes). The Et₂O washes were combined and concentrated under reduced pressure. Chromatography (SiO₂, 5 cm×15 cm, hexanes) afforded 8 as a clear, colorless oil (1.25 g, 1.69 g theoretical, 74.0%): ¹H NMR (CDCl₃, 250 MHz) δ3.64 (s, 3H, C(O)OCH₃), 3.38 (t, 2H, J =6.8 Hz, CH₂Br), 2.29 (t, 2H, J=7.4 Hz CH₂C(O)OCH₃), 1.83 (p, 2H, CH₂CH₂Br), 1.63 (m, 2H, CH₂CH₂C(O)OCH₃) 1.47–1.28 (m, 6H, alkyl protons).

methyl-8-triphenylphosphoranyl-octanoate-bromide (9). A solution of 8 (1.25 g, 5.23 mmol, 1.0 equiv.) in CH₃CN (4.0 mL, 1.31M) was treated with triphenylphosphine (1.50 g, 5.75 mmol, 1.1 equiv.) and stirred at reflux for 10 h. Additional triphenylphosphine (0.685 g, 2.61 mmol 0.5 equiv.) was added to the reaction mixture and stirring was continued at reflux for 5 h. The reaction mixture was concentrated under reduced pressure and washed repeatedly with Et₂O (5×10 mL washes). The remaining residue was then solubilized in the minimum volume of CH₂Cl₂ and concentrated under reduced pressure to afford 9 as a colorless foam (2.20 g, 2.61 g theoretical, 84.3%): 1H NMR (CDCl₃, 250 MHz)δ7.82–7.51 (m, 15H, ArH), 3.70–3.46 (m, 5H, CH₃OC(O)R and CH₂PPh₃), 2.13 (t, 2H, J=7.4 Hz, CH₂C(O)OCH₃), 1.62–1.43 (m, 6H, alkyl protons), 1.30–1.02 (m, 4H, alkyl protons); FABHRMS (NBA) m/e 419.2154 (C₂₇H₃₂BrO₂P-Br⁻ requires 419.2140).

methyl-cis-8,9-octadecenoate (10). A solution of 9 (0.71 g, 1.42 mmol, 1.0 equiv.) in THF (7.0 mL, 0.2M) at 25° C. was treated with KHMDS (3.0 mL, 0.5M solution in THF, 1.5 mmol, 1.06 equiv.) and the reaction mixture was stirred at reflux for 1 h. The reaction mixture was then cooled to −78° C., treated with decyl aldehyde (0.321 mL, 1.71 mmol, 1.2 equiv.) warmed to 25° C., and stirred for an additional 30 min. The reaction mixture was then treated with saturated aqueous NH₄Cl and partitioned between EtOAc (100 mL) and H₂O (100 mL). The organic layer was dried (Na₂SO₄) and concentrated under reduced pressure. Chromatography (SiO₂, 5 cm×15 cm, 0–2% EtOAc-hexanes gradient elution) afforded 10 as a colorless oil (0.290 g, 0.422 g theoretical, 68.7%): ¹H NMR (CDCl₃, 250 MHz) δ5.34 (m, 2H, CH═CH), 3.65 (s, 3H, CH₃OC(O)), 2.29 (t, 2H, J=7.4 Hz, CH₂C(O)OCH₃), 2.00 (m, 4H, CH₂CH═CHCH₂), 1.61 (m, 2H, CH₂CH₂C(O)OCH₃), 1.29 (bs, 20 H, alkyl protons), 0.86 (t, 3H, RCH₃).

cis-8,9 octadecenoic acid (11). A solution of 10 (0.245 g, 0.825 mmol, 1.0 equiv.) in THF-MeOH—H₂O (3-1-1 ratio, 4.1 mL, 0.2M) at 0° C. was treated with LiOH.H₂O (0.104 g, 2.48 mmol, 3.0 equiv.). The reaction mixture was warmed to 25° C., stirred for 8 h, and then partitioned between EtOAc (100 mL) and H$_2$O (100 mL). The organic layer was washed successively with 10% aqueous HCl (100 mL) and saturated aqueous NaCl (100 mL), dried, and concentrated under reduced pressure. Chromatography (SiO$_2$, 5 cm×15 cm, 10–30% EtOAc-hexanes gradient elution) afforded 11 as a colorless oil (0.156 g, 0.233 g theoretical, 67.0%): $^1$H NMR (CDCl$_3$, 250 MHz) δ5.34 (m, 2H, CH=CH), 2.34 (t, 2H, J=7.4 Hz, CH$_2$COOH), 2.01 (m, 4H, CH$_2$CH=CHCH$_2$), 1.61 (m, 2H, CH$_2$CH$_2$COOH), 1.47–1.23 (m, 20 H, alkyl protons), 0.87 (t, 3H, RCH$_3$).

18-Hemisuccinate-cis-9,10-octadecenoamide (12). A solution of 18 (0.047 g, 0.160M, 1.0 equiv) in CH$_2$Cl$_2$—CHCl$_3$ (3–1, 1.60 mL, 0.1M) was treated successively with Et$_3$N (0.045 mL, 0.320 mmol, 2.0 equiv), succinic anhydride (0.033 g, 0.320 mmol, 2.0 equiv) and DMAP (0.002 g, 0.016 mmol, 0.1 equiv), and the reaction mixture was stirred at 25° C. for 10 h. The reaction mixture was then partitioned between CH$_2$Cl$_2$ (50 mL) and H$_2$O (50 mL), and the organic layer was washed successively with 10% aqueous HCl (50 mL) and saturated aqueous NaCl (50 mL), dried (Na$_2$SO$_4$), and concentrated under reduced pressure. Chromatography (SiO$_2$, 3 cm×15 cm, 0–10% MeOH-EtOAc) afforded 12 as a white solid (0.051 g, 0.063 theoretical, 80.3%): $^1$H NMR (CDCl$_3$, 250 MHz) δ6.95 (b s, 1H, H$_2$NC(O)), 5.72 (b s, 1H, H$_2$NC(O)), 5.34 (m, 2H, CH=CH), 4.08 (t, 3H, J=6.6 Hz, CH$_2$OC(O)R), 2.61 (m, 4H, ROC(O)CH$_2$CH$_2$COOH), 2.21 (t, 2H, J=7.5 Hz, CH$_2$C(O)NH$_2$), 2.00 (m, 4H, CH$_2$CH=CHCH$_2$), 1.70–1.52 (m, 4H, CH$_2$CH$_2$C(O)NH$_2$ and CH$_2$CH$_2$OH), 1.29 (b s, 18H, alkyl protons); FAB-HRMS (NBA) m/e 398.2893 (C$_{22}$H$_{39}$NO$_5$+H$^+$ requires 398.2906).

methyl-9-bromo-nonanoate (13). A solution of methyl-9-hydroxy-nonanoate (1.1 g, 5.85 mmol, 1.0 equiv) in CH$_2$Cl$_2$ (30 mL, 0.2M) at 0° C. was treated successively with CBr$_4$ (2.5 g, 7.54 mmol, 1.3 equiv) and PPh$_3$ (2.15 g, 8.19 mmol. 1.4 equiv) and the reaction mixture was stirred at 4° C. for 10 h. The reaction mixture was then concencrtrated under reduced pressure and washed repeatedly with Et$_2$O (8×10 mL washes). The Et$_2$O washes were combined and concentrated under reduced pressure. Chromatography (SiO$_2$, 5 cm×15 cm, hexanes) afforded 13 as a clear, colorless oil (1.02 g, 1.47 g theorectical, 69.5%): $^1$H NMR (CDCl$_3$, 250 MHz) d 3.64 (s, 3H, C(O)OCH$_3$), 3.38 (t, 2H, J=6.8 Hz, CH$_2$Br), 2.29 (t, 2H, J=7.4 Hz CH$_2$C(O)OCH$_3$), 1.83 (p, 2H, CH$_2$CH$_2$Br), 1.63 (m, 2H, CH$_2$CH$_2$C(O)OCH$_3$) 1.47–1.28 (m, 8H, alkyl protons).

methyl-9-triphenylphosphoranyl-nonanoate-bromide (14). A solution of 13 (1.02 g, 4.06 mmol, 10 equiv) in CH$_3$CN (3.5 mL 1.16M) was treated with triphenylphosphine (1.17 g, 4.47 mmol, 1.1 equiv) and stirred at reflux for 10 h. Additional triphenylphosphine (0.532 g, 2.03 mmol, 0.5 equiv) was added to the reaction mixture and stirring was continued at reflux for 5 h. The reaction mixture was concentrated under reduced pressure and washed repeatedly with Et$_2$O (5×10 mL washes). The remaining residue was then solubilized in the minimum volume of CH$_2$Cl$_2$ and concentrated under reduced pressure to afford 14 as a colorless foam (1.90 g, 2.08 g theoretical, 91.3%): $^1$H NMR (CDCl$_3$, 250 MHz) δ7.82–7.51 (m, 15H, ArH), 3.70–3.46 (m, 5H, CH$_3$OC(O)R and CH$_2$PPh$_3$), 2.13 (t, 2H, J=7.4 Hz, CH$_2$C(O)OCH$_3$), 1.62–1.02 (m, 12H, alkyl protons); FAB-HRMS (NBA) m/e 433.2312 (C$_{28}$H$_{34}$BrO$_2$P–Br$^-$ requires 433.2296).

methyl-18-t-butyldiphenysilyloxy-cis-9,10 octadecenoate (15). A solution of 14 (1.0 g, 1.95 mmol, 1.0 equiv) in THF (6.5 mL, 0.3M) at 25° C. was treated with KHMDS (3.9 mL, 0.5M solution in THF, 1.95 mmol, 1.0 equiv) and the reaction mixture was stirred at reflux for 1 h. The reaction mixture was then cooled to −78° C., treated with 3 (0.93 g, 2.35 mmol, 1.2 equiv), warmed to 25° C., and stirred for an additional 30 min. The reaction mixture was then treated with saturated aqueous NH$_4$Cl and partitioned between EtOAc (100 mL) and H$_2$O (100 mL). The organic layer was dried (Na$_2$SO$_4$) and concentrated under reduced pressure. Chromatography (SiO$_2$, 5 cm×15 cm, 0–2% EtOAc-hexanes gradient elution) afforded 15 as a colorless oil (0.82 g, 1.07 g theoretical, 76.3%): $^1$H NMR (CDCl$_3$, 250 MHz) δ7.67 (m, 4H, ArH), 7.41 (m, 6H, ArH), 5.34 (m, 2H, CH=CH), 3.65 (m, 5H, CH$_3$OC(O) and CH$_2$OTBDPS), 2.29 (t, 2H, J=7.4 Hz, CH$_2$C(O)OCH$_3$), 2.00 (m, 4H, CH$_2$CH=CHCH$_2$), 1.55 (m, 4H, CH$_2$CH$_2$C(O)OCH$_3$ and CH$_2$CH$_2$OTBDPS), 1.29 (b s, 18H, alkyl protons), 1.04 (s, 9H, (CH$_3$)$_3$C).

18-T-butyldiphenylsilyloxy-cis-9,10-octadecenoic acid (16). A solution of 5 (0.81 g, 1.47 mmol, 1.0 equiv) in THF-MeOH—H$_2$O (3-1-1 ratio, 7.3 mL, 0.2M) at 0° C. was treated with LiOH.H$_2$O (0.188 g, 4.48 mmol, 3.0 equiv). The reaction mixture was warmed to 25° C., stirred for 8 h, and then partitioned between EtOAc (100 mL) and H$_2$O (100 mL). The organic layer was washed successively with 10% aqueous HCl (100 mL) and saturated aqueous NaCl (100 mL), dried, and concentrated under reduced pressure. Chromatography (SiO$_2$, 5 cm×15 cm, 10–30% EtOAc-hexanes gradient elution) afforded 16 as a colorless oil (0.700 g, 0.790 g theoretical, 88.7%): $^1$H NMR (CDCl$_3$, 250 MHz) δ7.67 (m, 4H, ArH), 7.41 (m, 6H, ArH), 5.34 (m, 2H, CH=CH), 3.65 (t, 3H, J=6.5 Hz, CH$_2$OTBDPS), 2.34 (t, 2H, J=7.4 Hz, CH$_2$COOH), 2.00 (m, 4H, CH$_2$CH=CHCH$_2$), 1.65–1.50 (m, 4H, CH$_2$CH$_2$COOH and CH$_2$CH$_2$OTBDPS), 1.47–1.23 (m, 18H, alkyl protons), 1.05 (s, 9H, (CH$_3$)$_3$C): FABHRMS (NBA/CsI) m/e 669.2772 (C$_{34}$H$_{52}$O$_3$Si+Cs$^+$ requires 669.2740).

18-T-butyldiphenylsilyloxy-cis-9,10-octadecenoamide (17). A solution of 16 (0.685 g, 1.98 mmol, 1.0 equiv) in CH$_2$Cl$_2$ (4.3 mL, 0.3M) at 0° C. was treated dropwise with oxalyl chloride (1.92 mL, 2M solution in CH$_2$Cl$_2$, 3.84 mmol, 3.0 equiv). The reaction mixture was stirred at 25° C. for 4 h, concentrated under reduced pressure, cooled to 0° C., and treated with saturated aqueous NH$_4$OH (2.0 mL). The reaction mixture was then partitioned between EtOAc (100 mL) and H$_2$O (100 mL), and the organic layer was dried (Na$_2$SO$_4$) and concentrated under reduced pressure. Chromatography (SiO$_2$, 5 cm×15 cm, 40–100% EtOAc-hexanes gradient elution) afforded 17 as a colorless oil (0.520 g, 0.684 g, 76.0%): $^1$H NMR (CDCl$_3$, 250 MHz) δ7.67 (m, 4H, ArH), 7.41 (m, 6H, ArH), 5.70–5.34 (m, 4H, H$_2$NC(O) and CH=CH), 3.65 (t, 3H, J=6.5 Hz, CH$_2$OTBDPS), 2.21 (t, 2H, J=7.5 Hz, CH$_2$C(O)NH$_2$), 2.00 (m, 4H, CH$_2$CH=CHCH$_2$), 1.65–1.50 (m, 4H, CH$_2$CH$_2$C(O)NH$_2$ and CH$_2$CH$_2$OTBDPS), 1.47–1.23 (m, 18H, alkyl protons), 1.05 (s, 9H, (CH$_3$)$_3$C); FABHRMS (NBA/CsI m/e 668.2929 (C$_{34}$H$_{53}$O$_2$NSi+Cs$^+$ requires 668.2900).

18-Hydroxy-cis-9,10-octadecenoamide (18). A solution of 17 (0.185 g, 0.345 mmol, 1.0 equiv) in THF (1.1 mL, 0.31M) was treated with tetrabutylammoniumfluoride (0.69 mL, 1.0M solution in THF, 0.69 mmol, 2.0 equiv) and the reaction mixture was stirred at 25° C. for 2 h. The reaction mixture was then partitioned between EtOAc (50 mL) and H$_2$O (50 mL), and the organic layer was dried (Na$_2$SO$_4$) and concentrated under reduced pressure Chromatography (SiO$_2$, 3 cm×15 cm, 0–5% MeOH-EtOAc gradient elution) afforded 18 as a white solid (0.097 g, 0.103 g theoretical, 94.6%): $^1$H NMR (CDCl$_3$, 250 MHz) δ5.65–5.34 (m, 4H, H$_2$NC(O) and CH=CH), 3.62 (t, 3H, J=6.5 Hz, CH$_2$OH), 2.21 (t, 2H, J=7.5 Hz, CH$_2$C(O)NH$_2$), 2.00 (m, 4H, CH$_2$CH=CHCH$_2$), 1.65–1.50 (m, 4H, CH$_2$CH$_2$C(O)NH$_2$ and CH$_2$CH$_2$OH), 1.29 (b s, 18H, alkyl protons); FAB-HRMS (NBA) 298.2732 (C$_{18}$H$_{35}$NO$_2$+H$^+$ requires 298.2746).

4. A method for inducing sleep as described in claim 3 wherein the unsaturation of the alkyl chain has a cis configuration.

5. A method for inducing sleep as described in claim 3 wherein the unsaturation of the alkyl chain has a trans configuration.

What is claimed is:

1. A method for inducing sleep comprising the step of administering a fatty acid primary amide to a subject.

2. A method for inducing sleep as described in claim 1 wherein the fatty acid primary amide includes an alkyl chain having an unsaturation.

3. A method for inducing sleep as described in claim 2 wherein the fatty acid primary amide has the following formula:

6. A method for inducing sleep as described in claim 3 wherein the fatty acid primary amide is cis-9,10-octadecenoamide.

7. A method for inducing sleep as described in claim 3 wherein the fatty acid primary amide is trans-9,10-octadecenoamide.

8. A method for inducing sleep as described in claim 3 wherein the fatty acid primary amide is cis-8,9-octadecenoamide.

9. A method for inducing sleep as described in claim 3 wherein the fatty acid primary amide is cis-11,12-octadecenoamide.

10. A method for inducing sleep as described in claim 3 wherein the fatty acid primary amide is cis-13,14-docosenoamide.

11. A method for inducing sleep as described in claim 1 wherein the fatty acid primary amide is administered by a method selected from the group of methods consisting of intraperitoneal injection (ip), subcutaneous injection (sc), intramuscular injection (im), peroral ingestion (po), spinal injection, and cranial injection.

12. A method for inducing sleep as described in claim 1 wherein the dosage ranges from 1 milligram to 10 grams per day.

* * * * *